(12) United States Patent
Chaudhari et al.

(10) Patent No.: US 6,331,502 B1
(45) Date of Patent: Dec. 18, 2001

(54) CATALYST SYSTEM CONTAINING A SEMILABILE ANIONIC LIGAND AND A USE OF SUCH CATALYST SYSTEM TO PRODUCE α, β, -UNSATURATED CARBOXYLIC ACIDS AND THEIR ESTERS

(75) Inventors: Raghunath Vitthal Chaudhari; Jayasree Puthenmadathil; Sunil Purushotham Gupte, all of Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/316,022

(22) Filed: May 21, 1999

(30) Foreign Application Priority Data

Dec. 9, 1998 (IN) ...................................... 3693/98

(51) Int. Cl.$^7$ .............................. B01J 31/00; B01J 27/14; B01J 27/185; B01J 23/42
(52) U.S. Cl. ......................... 502/162; 502/164; 502/167; 502/172; 502/208; 502/213; 502/339
(58) Field of Search .................................. 502/162, 164, 502/167, 172, 208, 213, 339; 560/100, 104–106, 205–207

(56) References Cited

U.S. PATENT DOCUMENTS

| | | | |
|---|---|---|---|
| 3,904,672 | * | 9/1975 | Knifton .......................... 260/486 AC |
| 3,952,034 | * | 4/1976 | Thompson et al. ................ 260/410.5 |
| 4,257,973 | * | 3/1981 | Mrowca ........................ 260/410.9 R |
| 4,284,585 | * | 8/1981 | Pugach .................................. 562/891 |
| 4,334,094 | * | 6/1982 | Knifton ................................. 562/517 |
| 4,599,476 | * | 7/1986 | Drent ..................................... 585/511 |
| 5,166,116 |   | 11/1992 | Drent et al. .......................... 502/167 |
| 5,177,253 | * | 1/1993 | Drent et al. .......................... 560/207 |
| 5,482,596 | * | 1/1996 | Wu ........................................ 562/406 |
| 5,731,255 | * | 3/1998 | Pan et al. ............................. 502/155 |
| 5,869,738 | * | 2/1999 | Pan et al. ............................. 560/207 |
| 6,069,253 | * | 5/2000 | Chaudhari et al. ...................... 546/2 |
| 6,103,927 | * | 8/2000 | De Castro Loureiro Barreto Rosa et al. ........................... 560/207 |

OTHER PUBLICATIONS

A. Scrivanti et al., "A Convenient Synthesis of 2–(6–Methoxy–2–Naphthyl)Propenoic Acid (A Naproxen Precursor)," *Tetrahedron Letters*, vol. 36, pp. 9015–9018, Oct. 1995.

D. Zargarian et al., "Palladium–Catalyzed Hydrocarboxylation of Alkynes With Formic Acid," *Organometallics*, vol. 12, No. 3, pp. 712–724, Sep. 1992.

Y. Kushino et al., "Palladium–Catalyzed Hydroesterification of Alkynes in the Presence of P–Toluenesulfonic Acid Under A Normal Pressure of Carbon Monoxide," *Journal of Molecular Catalysis*, 89, pp. 151–158, Dec. 1993.

\* cited by examiner

*Primary Examiner*—Mark L. Bell
*Assistant Examiner*—Patricia L. Hailey
(74) *Attorney, Agent, or Firm*—Fitzpatrick, Cella, Harper & Scinto (57) ABSTRACT

The present invention relates to a novel catalyst system comprising a palladium metal source, a monodentate phosphorus ligand, anionic semilabile ligand, protonic acid, and proton source, and an improved process for the preparation of α,β-unsaturated carboxylic acids and their esters represented as

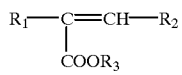

comprising the steps of reacting alkynes in an aprotic organic solvent, in the presence of said novel catalyst system, in carbon monoxide atmosphere in a homogeneous medium, cooling the reaction mixture to ambient temperature, flushing the reaction vessel with inert gas, removing the solvent by conventional methods, separating the catalyst and isolating the α,β-unsaturated carboxylic acids and their esters by conventional methods.

29 Claims, 1 Drawing Sheet

Fig 1: Alkynes of Formula I $$R_1 - C \equiv C - R_2$$

Fig 2: α,β,Unsaturated carboxylic acids and esters of Formula II $$R_1 - \underset{COOR_3}{C} = CH - R_2$$

CATALYST SYSTEM CONTAINING A SEMILABILE ANIONIC LIGAND AND A USE OF SUCH CATALYST SYSTEM TO PRODUCE α, β, -UNSATURATED CARBOXYLIC ACIDS AND THEIR ESTERS

FIELD OF THE INVENTION

The present invention relates to a novel catalyst system useful for the preparation of α,β-unsaturated carboxylic acids and their esters. Further, it also relates to an improved process for the conversion of acetylenically unsaturated compounds to corresponding α,β-unsaturated carboxylic acids and their esters represented by the formula II given below, using the said catalyst system.

wherein $R_1$ and $R_2$ are hydrogen, alkyl, aryl, arylalkyl, cycloaliphatic groups with or without substituents and $R_3$ is hydrogen in the case of acids and may be alkyl, aryl, arylalkyl, cycloaliphatic groups with or without substituents in the case of esters.

BACKGROUND OF THE INVENTION

The α,β-unsaturated carboxylic acids and esters have a variety of applications in industries as intermediates in optically active anti-inflammatory drugs, monomers for polymer synthesis, finechemicals etc.

The prior art describes improved process as catalyst systems for employment in improved processes for the preparation of α,β-unsaturated carboxylic acids and esters. The best known of such catalysts are homogeneous palladium catalysts. Zagarian and Alper, Organometallics 1993, 12,712–724 disclosed palladium catalyst hydrocarboxylation of alkynes with formic acid. The catalyst system used in said improved process contained a palladium complex such as palladium acetate, mono as well as diphosphine ligands and formic acid. Even though the improved process required only mild reaction conditions, the conversion rates and product selectivity were low.

U.S. Pat. Nos. 5,166,116 and 5,177,253 describe improved processes for the hydrocarbonylation of alkynes employing a catalyst system consisting of a group VIII metal cation, a source of organic diphosphine having at least one of the phosphorous atoms substituted by an aromatic substituent containing an imino nitrogen atom and a source of an anion. These improved processes give high conversions to a α,β-unsaturated carboxylic acid esters and good selectivity to iso products, but need severe reaction conditions like a carbon monoxide pressure of 60 atm and use of excess ligands and acid promoters. Another disadvantage of this catalyst system, is the complexity involved in the synthesis of the ligands used, which requires a multistep improved process which requires drastic reaction conditions and is required to be handled strictly under inert atmosphere. Kushino et. al. J. Mol Cat., 89, 1994, 151–158 disclosed the use of a catalyst system comprising palladium bisdibenzilidine complex, triphenyl phosphine and para toluenesulphonic acid for the hydroesterification of alkynes under mild conditions. But their reaction rates and product selectivity were also poor.

Later, A. Scrivanti and U. Matteoli, Tet, lett., 36, 1995, 9015–9018 carried out the hydrocarbonylation of phenyl acetylene and 6-methoxy-2-naphthyl ethyne to corresponding α,β-unsaturated carboxylic acids using the same catalyst system in the U.S. Pat. Nos. 5,166,116 and 5,177,253. This improved process gives good rates and selectivity to the 2-substituted α,β-unsaturated carboxylic acids but uses excess ligands and promoters and again the complexities involved in the synthesis of the ligand used are an added disadvantage.

Thus, most of these catalyst systems have several disadvantages in their employment for the carbonylation of alkynes. These disadvantages include the requirement of severe conditions, use of excess ligands and promoters, complexity in ligand synthesis and very low conversion and selectivity. In general, various catalyst systems used for the hydrocarbonylation of alkynes contain a palladium source, a phosphine ligand and an acid promoter.

The applicants have observed during the course of their studies that the use of a palladium source along with a semilabile anionic ligand which is a chelating organic compound containing a N donor and an O group, a monodenate phosphorous ligand and a protonic acid provides an improved catalyst system for the hydrocarbonylation of acetylenically unsaturated compounds to α,β-unsaturated carboxylic acids and esters. The use of such a catalyst gives high yield and selectivity under normal pressure of carbon monoxide.

OBJECTS OF THE INVENTION

The object of the present invention, is to provide a novel catalyst system and an improved process for the carbonylation of alkynes providing high selectivity to 2-substituted α,β-unsaturated carboxylic acids and esters under normal pressure of carbon monoxide.

SUMMARY OF THE INVENTION

Figure 1:
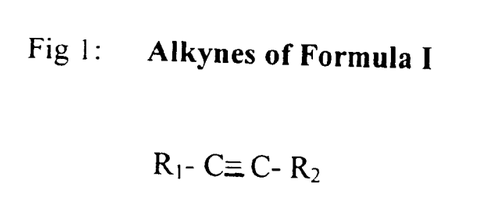
FIG. 1 represents the general formula for alkynes.
Figure 2:
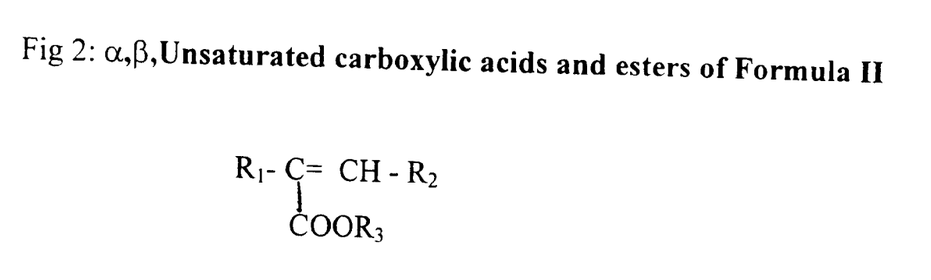
FIG. 2 represents the general formula of the α,βunsaturated carboxylic acids and their esters.

The invention provides a novel catalyst system comprising (a) source of palladium metal (b) a monodenate phosphorous ligand (c) anionic semilabile chelating ligand (d) protonic acid and (e) proton source. The said catalyst system is useful in the preparation of α,β-unsaturated carboxylic acids and their esters. Further, the invention provides an improved process for the synthesis of α,β-unsaturated carboxylic acids and esters using the said catalyst, comprising the steps of reacting the alkynes (represented by formula I) shown hereinbelow with a compound in an aprotic organic solvent, in the presence of the catalyst system, in carbonmonoxide atmosphere in a homogenous medium, cooling the reaction mixture to ambient temperature, flushing the reaction vessel with inert gas, removing the solvent by conventional methods, separating the catalyst and isolating the α,β-unsaturated carboxylic acids and their esters by conventional methods.

DETAILED DESCRIPTION OF THE INVENTION

Accordingly, the present invention provides a novel catalyst system useful for the synthesis of α,β-unsaturated carboxylic acids and their esters and an improved process for the preparation α,β-unsaturated carboxylic acids and their esters, which are represented by the general formula II:

wherein $R_1$ and $R_2$ is hydrogen, alkyl, aryl, arylalkyl, cycloaliphatic groups with or without substituents and $R_3$ are hydrogen in the case of acids and may be alkyl, aryl, arylalkyl, cycloaliphatic groups with or without substituents in the case of esters.

The said catalyst system comprises:
(a) a palladium metal source;
(b) monodentate phosphorous ligand;
(c) an anionic semilabile ligand being an organic compound containing a N donor and an O⁻ group;
(d) protonic acid;
(c) proton source.

wherein, the ratio of Palladium:anionic semilabile ligand:phosphorous:protonic acid is in the range of 1:2:4:10 to 1:15:30:40.

Particularly, this invention relates to the employment of said efficient catalyst system, which contains a semilabile anionic ligand which is a chelating organic compound containing a N donor and an O⁻ group, for the hydrocarbonylation of alkynes under normal pressure of carbon monoxide. In general, the alkynes which can be converted to corresponding α,β-unsaturated carboxylic acids and esters, include any of the alkynes, having a general formula I given below:

wherein $R_1$ and $R_2$ have the meaning defined above.

In one of the embodiments of the present invention, the compound containing palladium or palladium metal source is selected from the group consisting of palladium acetate, palladium chloride, palladium acetylacetonate and tetrakistriphenylphosphino palladium, bis(disbenzylidene acetone) palladium.

In another embodiment, the anionic semilabile chelating ligand may be an organic compound containing a N donor and an O⁻ group exemplified by pyridine carboxylic acids, 2-hydroxypyrridine, 2-(2'-hydroxyethyl pyrridine), pyridil-2, pyridil-3, piperidil-2, pyrridine, piperidine carboxylic acids exemplified by quinolyl-2-, isoquinolyl-3-carboxylic acids, particularly pyridil-2-, pyridil-3, piperidil-carboxylic acids and 8-hydroxy quinoline.

In yet another embodiment the phosphorous ligand may be any of the mono phosphines or phosphites or a member of their family. Preferably phosphines such as triphenyl phosphine, tris paratolyl phosphine, trisparachlorophenyl phosphine, tris paramethoxyphenyl phosphine, tricyclohexylphosphine, tributylphosphine, triphenyl phosphite, tributyl phosphine, tris para fluorophenyl phosphine, tributyl phosphite may be used.

In still another embodiment, the acid promoter may be any protonic acids of the kind para tolune sulphonic acid, methane sulphonic acid, triflouro methan sulphonic acid, acetic acid, formic acid, oxalic acid and triflouro acetic acid.

In another embodiment the proton source may be water, formic acid, acetic acid and propionic acid for the preparation of the α,β-unsaturated acids and any alcohol like methanol, ethanol, butanol or phenols for the preparation of the α,β-unsaturated esters.

In another embodiment, the concentration of palladium compound in the catalyst system may be 1 mole of palladium compound for every 100 to 5000 moles of alkyne, preferably 1 mole of palladium compound for every 200 to 1000 moles of alkyne.

In another embodiment, the number of moles of the anionic semilabile ligand per gram atom of palladium in the catalyst system may be in the range of 1 to 100 moles preferably 2 to 20.

In still another embodiment, the number of moles of acid promoter per gram atom of palladium in the catalyst system may be in the range of 1 to 100 moles preferably 10 to 40 in the case of preparation of α,β-unsaturated esters and preferably 30-50 in the case of preparation of α,β-unsaturated acids.

In yet another embodiment the ratio of number of moles of the mono phosphorous ligand per gram of palladium in the catalyst system may be in the range of 1-100 moles, preferably 4 to 40.

In another embodiment the ratio of number of moles of proton source per mole of the alkyne may be in a range 1 to 50 moles, preferably 2 to 10.

In yet another embodiment the ratio of number of moles of the protonic acid in the catalyst system may be in the range of 1-100 moles, preferably 10 to 40.

Further, the invention relates to an improved process for the synthesis of α,β-unsaturated carboxylic acids and their esters, represented by the formula:

wherein $R_1$ and $R_2$ is hydrogen, alkyl, aryl, arylalkyl, cycloaliphatic groups with or without substituents and $R_3$ is hydrogen in the case of acids and may be alkyl, aryl, arylalkyl, cycloaliphatic groups with or without substituents in the case of esters; said process comprising the steps of reacting an acetylynically unsaturated compound with a compound containing palladium, in presence of said novel catalyst system comprising an anionic semilabile ligand, a monodentate phosphorous ligand, an acid promoter and a proton source, in an aprotic organic solvent in carbon monoxide atmosphere in a homogeneous medium at a temperature ranging between 30 to 120° C., for a period ranging between 30 to 120 minutes at ambient pressure, cooling the reaction mixture to ambient temperature, flushing the reaction vessel with inert gas removing the solvent by conventional methods, separating the catalyst and isolating the compound of general formula II, i.e. the unsaturated carboxylic acids and their esters.

In an embodiment, phenyl acetylene may be reacted with carbon monoxide in the presence of said catalyst system to obtain 2-phenyl propenic acid and 2-phenyl propenoates. However, it must be understood that the process is applicable to other alkynes also.

In yet another embodiment, the aprotic organic solvent may be selected from the group of aromatic hydrocarbons comprising benzene, toluene, xylenes, or from the group of ketones comprising methyl ethyl ketone, acetone or from the group of amides comprising N-methyl pyrrolidone or from the group of cyclic esters comprising tetrahydrofuran, dioxane or from the group of nitriles comprising acetonitrile or from the group of carboxylic acids comprising formic acid, acetic acid and propionic acid for the preparation of α,β-unsaturated acids.

In another embodiment, the alcohol may itself act as the proton source.

In a further embodiment, the aprotic organic solvent may be selected from the group of aromatic hydrocarbons comprising benzene, toluene, xylenes, or from the group of ketones comprising methyl ethyl ketone, acetone or from the group of amides comprising N-methyl pyrrolidone or from the group of cyclic ethers comprising tetrahydrofuran and dioxan for the preparation of the α,β-unsaturated esters.

In the feature of the invention the said reaction can be conveniently carried out in a stirred reactor with the improved catalyst employed in homogeneous phase with a suitable solvent in presence of carbon monoxide and at atmospheric pressure.

In yet another feature, the ambient pressure for the reaction is 5–100 psig.

In another feature, the reaction is carried out in a homogeneous medium, wherein the catalyst components and the reactants are dissolved in the solvent and the reaction takes place in the solution.

The improved process for the preparation of α,β-unsaturated acids and their esters, the present invention is described herein below with examples which are illustrative only and should not be construed to limit the scope of the present invention in any manner.

Examples 1 to 8 pertain to the novel catalyst system and examples 9 to 19 pertain to the improved process.

EXAMPLE 1

A 300 ml stirred autoclave was charged with the following reactants:

Phenyl acetylene: 0.039 mols

Pd(OAC)$_2$: 1.94×10$^{-4}$ mols

2-Picolinic acid: 2.91×10$^{-3}$ mols

Triphenyl phosphine: 6.97×10$^{-3}$ mols

Para-toulene sulphonic acid: 7.76×10$^{-3}$ mols

Butanol: 0.161 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromotography. The GC analysis showed initial TOF of 2500h$^{-1}$ and 95% conversion of phenylacetylene with 98% selectivity to butyl 2-phenyl propenoate.

The product was then isolated by removing the solvents and remaining phenyl acetylene by distillation and passing a solution of the resulting mixture of products and catalyst through a glass column filled with activated alumina thereby removing the catalyst and any other ingredients in the mixture.

EXAMPLE 2

A 300 ml stirred autoclave was charged with the following reactants

Phenyl acetylene: 0.039 mols

Pd(acac)$_2$: 1.94×10$^{-4}$ mols

2-Picolinic acid: 2.91×10$^{-3}$ mols

Triphenylphosphine: 6.79×10$^{-3}$ mols

Para toluene sulphonic acid: 7.76×10$^{-3}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 2400h$^{-1}$ and 95% conversion of phenylacetylene with 98% selectivity to butyl 2-phenyl propenoate.

The product was then isolated by removing the solvents and remaining phenyl acetylene by distillation and passing a solution of the resulting mixture of products and catalyst through a glass column filled with activated alumina thereby removing the catalyst and any other ingredients in the mixture.

EXAMPLE 3

A 300 ml stirred autoclave was charged with the following reactants

Phenyl acetylene: 0.039 mols

Pd(dha)$_2$: 1.94×10$^{-4}$ mols

2-Picolinic acid: 2.91×10$^{-3}$ mols

Triphenylphosphine: 6.79×10$^{-3}$ mols

Para toluene sulphonic acid: 7.76×10$^{-3}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of $2500h^{-1}$ and 95% conversion of phenylacetylene with 98% selectivity to butyl 2-phenyl propenoate.

The product was then isolated by removing the solvents and remaining phenyl acetylene by distillation and passing a solution of the resulting mixture of products and catalyst through a glass column filled with activated alumina thereby removing the catalysts and any other ingredients in the mixture.

EXAMPLE 4

A 300 ml stirred autoclave was charged with the following reactants

Phenyl acetylene: 0.039 mols $Pd(OAC)_2$: $1.94 \times 10^{-4}$ mols

2-Picolinic acid: $2.91 \times 10^{-3}$ mols

Tris P-fluoro phenylphosphine: $6.79 \times 10^{-3}$ mols

Para toluene sulphonic acid: $7.76 \times 10^{-3}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of $3500h^{-1}$ and 97% conversion of phenylacetylene with 98% selectivity to butyl 2-phenyl propenoate.

The product was then isolated by removing the solvents and remaining phenyl acetylene by distillation and passing a solution of the resulting mixture of products and catalyst through a glass column filled with activated alumina thereby removing the catalyst and any other ingredients in the mixture.

5) Examples for Different $R_1$, $R_2$ in the Substrate

EXAMPLE 5

A 300 ml stirred autoclave was charged with the following reactants

Ethynyl toluene: 0.039 mols $Pd(OAC)_2$: $1.94 \times 10^{-4}$ mols

2-Picolinic acid: $2.91 \times 10^{-3}$ mols

Triphenylphosphine: $6.79 \times 10^{-3}$ mols

Para toluene sulphonic acid: $7.76 \times 10^{-3}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, 4-ethynyl toluene and butanol came in contact under reaction conditions in the presence of carbon monoxide in the gaseous phase.

For preparation of final butyl-2-(4-tolyl)-propenoate product, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of $2300h^{-1}$ and 95% conversion of 4-ethynyl toluene with 97% selectivity to butyl 2-(4-tolyl) propenoate.

The product was then isolated by removing the solvents and remaining 4-ethynyl toluene by distillation and passing a solution of the resulting mixture of products and catalyst through a glass column filled with activated alumina thereby removing the catalyst and any other ingredients in the mixture.

EXAMPLE 6

A 300 ml stirred autoclave was charged with the following reactants 1-ethynyl cyclohexene: 0.039 mols $Pd(OAC)_2$: $1.94 \times 10^{-4}$ mols 2-Picolinic acid: $2.91 \times 10^{-3}$ mols Triphenylphosphine: $6.79 \times 10^{-3}$ mols Para toluene sulphonic acid: $7.76 \times 10^{-3}$ mols Butanol: 0.162 mols Toluene (solvent): 0.652 mols The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol were came in contact under reaction conditions in the presence of carbon monoxide in the gaseous phase.

For preparation of final butyl-2-(cyclohexenyl) propenoate product, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of $250h^{-1}$ and 95% conversion of 1-ethynyl cyclohexene with 96% selectivity to butyl 2-cyclohexenyl propenoate.

The product was then isolated by removing the solvents and remaining 1-ethynyl cyclohexene by distillation and passing a solution of the resulting mixture of products and catalyst through a glass column filled with activated alumina thereby removing the catalyst and any other ingredients in the mixture.

EXAMPLE 7

A 3(K) ml stirred autoclave was charged with the following reactants

1-Phenyl-1-propyne: 0.039 mols $Pd(OAC)_2$: $1.94 \times 10^{-4}$ mols

2-Picolinic acid: $2.91 \times 10^{-3}$ mols

Triphenylphosphine: $6.79 \times 10^{-3}$ mols

Para toluene sulphonic acid: $7.76 \times 10^{-3}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, 1-phenyl-1-propyne and butanol came in contact with reaction conditions in the presence of carbon monoxide in the gaseous phase.

For preparation of final ester products, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF at 300 $h^{-1}$ and 90% conversion of 1-phenyl-1-propyne with 47% selectivity to butyl-3-methyl-2-phenyl propenoate and 53% selectivity to butyl-2-methyl-3-phenyl propenoate The product was then isolated by removing the solvents and remaining phenyl acetylene by distillation and passing a solution of the resulting mixture of products and catalyst through a glass column filled with activated alumina thereby removing the catalyst and any other ingredients in the mixture.

EXAMPLE 8

A 300 ml stirred autoclave was charged with the following reactants

Propargyl alcohol: 0.039 mols $Pd(OAC)_2$: $1.94 \times 10^{-4}$ mols

2-Picolinic acid: $2.91 \times 10^{-3}$ mols

Triphenylphosphine: $6.79 \times 10^{-3}$ mols

Para toluene sulphonic acid: $7.76 \times 10^{-3}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol came in contact under reaction conditions in the presence of carbon monoxide in the gaseous phase.

For preparation of final ester products, the pressure in the autoclave was maintained constant (the total pressure was around 40 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 100 $h^{-1}$ and 95% conversion of phenylacetylene with 85% selectivity to butyl 2-(hydroxymethyl) propenoate and 15% butyl-3-(hydroxymethyl) propenoate.

The product was then isolated by removing the solvents and remaining phenyl acetylene by distillation and passing a solution of the resulting mixture of products and catalyst through a glass column filled with activated alumina thereby removing the catalyst and any other ingredients in the mixture.

EXAMPLE 9

A 300 ml stirred autoclave was charged with the following reactants;

Phenyl accetylene: 0.039 mols $Pd(OAc)_2$: $1.94 \times 10^{-4}$ mols

2-Picolinic acid: $3.88 \times 10^{-4}$ mols

Triphenylphosphine: $7.76 \times 10^{-4}$ mols

Para toluene sulphonic acid: $3.88 \times 10^{-4}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, phenylacetylene and butanol were came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled showed initial TOF (turn over frequency) of 600 $h^{-1}$ and 50% conversion of phenyl acetylene with 98% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingredients in the mixture.

EXAMPLE 10

A 300 ml stirred autoclave was charged with the following reactants

Phenyl acetylene: 0.039 mols $Pd(OAc)_2$: $1.94 \times 10^{-4}$ mols

2-Pipecolinic acid: $3.88 \times 10^{-4}$ mols

Triphenylphosphine: $7.76 \times 10^{-4}$ mols

Para toluene sulphonic acid: $3.88 \times 10^{-4}$ mols

Butanol: 0.162 mols

Toluene (solvent): 0.652 mols

The contents of the autoclave were flushed with nitrogen and then many times with carbon monoxide. Thereafter, the contents heated to 100° C. After the temperature attained, stirring started and it was observed that carbon monoxide absorption commenced immediately. This confirmed that the active catalyst for the carbonylation reaction was formed in situ instantaneously when the contents of the reactor palladium acetate, 2-pipecolinic acid, para toluene acetic acid, triphenyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 600 $h^{-1}$ and 50% conversion of phenyl acetylene with 98% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingredients in the mixture.

EXAMPLE 11

A 300 ml stirred autoclave was charged with the following reactants

Phenyl acetylene: 0.039 mols $Pd(OAc)_2$: $1.94 \times 10^{-4}$ mols 8-hydroxyquinoline: $3.88 \times 10^{-4}$ mols Triphenylphosphine: $7.76 \times 10^{-4}$ mols Para toluene sulphonic acid: $3.88 \times 10^{-4}$ mols Butanol: 0.162 mols Toluene (solvent): 0.652 mols The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 8-hydroxy quinoline, para toluene acetic acid, triphenyl phosphine, phenylacetylene and butanol were came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 300 $h^{-1}$ and 25% conversion of phenyl acetylene with 85% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingredients in the mixture.

EXAMPLE 12

A 300 ml stirred autoclave was charged with the following reactants

Phenyl acetylene: 0.039 mols $Pd(OAc)_2$: $1.94 \times 10^{-4}$ mols

2-Picolinic acid: $3.88 \times 10^{-4}$ mols

Tris para chlorophenylphosphine: $7.76 \times 10^{-4}$ mols

Para toluene sulphonic acid: $3.88 \times 10^{-4}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, tris para chlorophenyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 700 $h^{-1}$ and 98% conversion of phenyl acetylene with 98% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingradients in the mixture.

EXAMPLE 13

A 300 ml stirred autoclave was charged with the following reactants

Phenyl acetylene: 0.039 mols $Pd(OAc)_2$: $1.94 \times 10^{-4}$ mols

2-Picolinic acid: $3.88 \times 10^{-4}$ mols

Tris paratolyl phosphine: $7.76 \times 10^{-4}$ mols

Para toluene sulphonic acid: $3.88 \times 10^{-4}$ mols

Butanol: 0.162 mols

Toluene (solvent): 0.652 mols

The contents of the autoclave were flushed with nitrogen and then many times with carbon monoxide. Thereafter, the contents were heated to 100° C. After the temperature was attained, stirred started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, tris paratolyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 650 $h^{-1}$ and 60% conversion of phenyl acetylene with 98% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingradients in the mixture.

EXAMPLE 14

A 300 ml stirred autoclave was charged with the following reactants

Phenyl acetylene: 0.039 mols
$Pd(OAc)_2$: $1.94 \times 10^{-4}$ mols
2-Picolinic acid: $3.88 \times 10^{-4}$ mols
Tributyl phosphine: $7.76 \times 10^{-4}$ mols
Para toluene sulphonic acid: $3.88 \times 10^{-4}$ mols
Butanol: 0.162 mols
Toluene (solvent): 0.652 mols The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, tributyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 130 $h^{-1}$ and 10% conversion of phenyl acetylene with 94% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingradients in the mixture.

EXAMPLE 15

A 300 ml stirred autoclave was charged with the following reactants

Phenyl acetylene: 0.039 mols
$Pd(OAc)_2$: $1.94 \times 10^{-4}$ mols
2-Picolinic acid: $3.88 \times 10^{-4}$ mols
Tri cyclohexyl phosphine: $7.76 \times 10^{-4}$ mols
Para toluene sulphonic acid: $3.88 \times 10^{-4}$ mols
Butanol: 0.162 mols
Toluene (solvent): 0.652 mols The contents of the autoclave were flushed with nitrogen and then many times with carbon monoxide. Thereafter, the contents were heated to 100° C. After the temperature was attained, stirred started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, tricyclohexyl phosphine, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was around 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 20 $h^{-1}$ and 3% conversion of phenyl acetylene with 92% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingradients in the mixture.

EXAMPLE 16

A 300 ml stirred autoclave was charged with the following reactants

Phenyl acetate: 0.039 mols
$Pd(OAc)_2$: $1.94 \times 10^{-4}$ mols
2-Picolinic acid: $3.88 \times 10^{-4}$ mols
Triphenylphosphite: $7.76 \times 10^{-4}$ mols
Para toluene sulphonic acid: $3.88 \times 10^{-4}$ mols
Butanol: 0.162 mols
Toluene (solvent): 0.652 mols The contents of the autoclave were flushed with nitrogen and then many times with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reaction palladium acetate, 2-picolinic acid, para toluene acetic acid, triphenyl phosphite, phenylacetylene and butanol came in contact under reaction conditions in the presence of carbon monoxide in the gaseous phase.

For preparation of final butyl-2-phenylpropenoate product, the pressure in the autoclave was maintained constant (the total pressure was about 15 psig at 100° C. when the reaction started) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 120 $h^{-1}$ and 10% conversion of phenyl acetylene with 94% selectivity to butyl-2-phenyl propenoate.

The product was then isolated by removing the solvents and remaining phenylacetylene by distillation and passing a solution of the resulting mixture of products and catalyst through a glass column filled with activated alumina thereby removing the catalyst and any other ingradients in the mixture.

EXAMPLE 17

A 300 ml stirred autoclave was charged with the following reactants 1,2-diphenyl acetylene: 0.039 mols
$Pd(OAc)_2$: $1.94 \times 10^{-4}$ mols
2-Picolinic acid: $3.88 \times 10^{-4}$ mols
Triphenylphosphine: $7.76 \times 10^{-4}$ mols
Para toluene sulphonic acid: $3.88 \times 10^{-4}$ mols
Butanol: 0.162 mols
Toluene (solvent): 0.652 mols The contents of the autoclave were flushed with nitrogen and then twice with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene acetic acid, triphenyl phosphine, 1,2-diphenylacetylene and butanol came in contact under reaction conditions in the presence of carbon monoxide in the gaseous phase.

For preparation of final butyl-2,3-diphenylpropenoate product, the pressure in the autoclave was maintained constant at 15 psig (total pressure) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 200 $h^{-1}$ and 20% conversion of 1,2-diphenylacetylene with 100% selectivity to butyl-2,3-diphenyl propenoate.

The product was then isolated by removing the solvents by distillation and passing a solution of the resulting mixture of products and catalyst through a glass column filled with activated alumina thereby removing the catalyst and any other ingradients in the mixture. The substrate remained and was separated column chromatography.

EXAMPLE 18

A 50 ml stirred autoclave was charged with the following reactants

Phenyl acetylene: 0.0147 mols
$Pd(OAc)_2$: $7.2767 \times 10^{-5}$ mols
2-Picolinic acid: $1.433 \times 10^{-4}$ mols
Triphenylphosphine: $2.9 \times 10^{-4}$ mols
Formic acid: 0.022 mols
Toluene (solvent): 0.239 mols The contents of the autoclave were flushed with nitrogen and then twice with carbon monoxide. Thereafter, the contents were heated to 100° C. After the temperature was attained, stirring started and it was observed that carbon monoxide absorption commenced immediately. This confirmed that the active catalyst for the carbonylation reaction was formed insitu instantaneously when the contents of the reactor palladium acetate, 2-picolinic acid, formic acid triphenyl phosphine and phenylacetylene came in contact under reaction conditions in the presence of carbon monoxide in the gaseous phase.

For preparation of final 2-phenylpropenoic acid product, the pressure in the autoclave was maintained constant at 15 psig (total pressure) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 500 $h^1$ and 99% conversion of phenylacetylene with 96% selectivity to 2-phenyl propenoic acid.

The final reaction mixture was washed many times with water to remove formic acid and then extracted with 10% NaOH solution to get the sodium salt of 2-phenylpropenoic acid in the NaOH layer. The NaOH layer was separated and acidified with 10% HCl and extracted by diethyl ether which on subsequent evaporation gave the product as white crystals.

EXAMPLE 19

A 50 ml stirred autoclave was charged with the following reactants

Phenyl acetylene: 0.0147 mols
$Pd(OAc)_2$: $7.2767 \times 10^{-5}$ mols
2-Picolinic acid: $1.433 \times 10^{-4}$ mols
Triphenylphosphine: $2.9 \times 10^{-4}$ mols
p-toluene sulphonic acid: 0.0157 mols
Water: 0.027 mols
Acetone (solvent): 0.239 mols The contents of the autoclave were flushed with nitrogen and then twice with carbon monoxide. Thereafter, the contents were heated to 100° C. After the temperature was attained, stirring started and it was observed that carbon monoxide absorption commenced immediately. This confirmed that the active catalyst for the carbonylation reaction was formed in situ instantaneously when the contents of the reactor palladium acetate, 2-picolinic acid, para toluene sulphonic acid triphenyl phosphine and phenylacetylene came in contact under reaction conditions in the presence of carbon monoxide in the gaseous phase.

For preparation of final 2-phenylpropenoic acid product, the pressure in the autoclave was maintained constant at 15 psig (total pressure) and the progress of the reaction was monitored by observing the pressure drop and by liquid sampling. The reaction was continued until the pressure drop was too low. The reactor was then cooled and the liquid phase analysed by gas chromatography. The GC analysis showed initial TOF of 450 $h^{-1}$ and 99% conversion of phenylacetylene with 98% selectivity to 2-phenyl propenoic acid.

The final reaction mixture was washed many times with water to remove formic acid and then extracted with 10% NaOH solution to get the sodium salt of 2-phenylpropenoic acid in the NaOH layer. The NaOH layer was separated and acidified with 10% HCl and extracted by diethyl ether which on subsequent evaporation gave the product as white crystals.

Advantages of the invention
1. A novel and improved catalyst system for the preparation of α,β-unsaturated carboxylic acids and their esters.
2. Provides high reaction rates and high selectivity to the 2-substituted α,β-unsaturated carboxylic acids and their esters under ambient pressure of carbon monoxide.
3. Use of simple ligands which are easily available in the market and are cheap.
4. Avoids use of excess ligands and promoters.

What is claimed is:
1. A novel catalyst system for converting alkynes to α,β-unsaturated acids and their esters, the catalyst system comprising:

(a) a palladium metal source;
(b) a monodentate phosphorus ligand;
(c) anionic semilabile chelating ligand containing N-donor and an O group selected from the group consisting of 2-hydroxy pyrridine, (2-(2'-hydroxy ethyl pyrridine), pyridil-3, piperidil-2, quinolyl-2, isoquinolyl-3-carboxylic acids, pyridil-2, piperidil-2-carboxylic acids, 8-hydroxy quinoline, and pyridine carboxylic acid;
(d) acid promoter; and
(e) proton source;
wherein the ratio of palladium:anionic semilabile ligand:phosphorous:acid promoter is in the range of 1:2:4:10 to 1:15:30:40.

2. A catalyst system as claimed in claim 1 wherein, the compound containing palladium is selected from the group consisting of palladium acetate, palladium chloride, palladium bromide, palladium iodide, palladium acetylacetonate, tetrakistriphenylphosphino palladium and bis (dibenzyleidene acetone) palladium.

3. A catalyst system as claimed in claim 1 wherein the phosphorus ligand is selected from the group consisting of mono phosphines or phosphites or members of their families.

4. A catalyst system as claimed in claim 1 wherein the phosphorus ligand used is selected from the group consisting of triphenyl phosphine, tris paratolyl phosphine, tris para chlorophenyl phosphine, tris paramethoxyphenyl phosphine, tricyclohexyl phosphine, tributyl phosphine, triphenyl phosphite, tributyl phosphite and tris parafluorophenyl phosphine.

5. A catalyst system as claimed in claim 1 wherein the acid promoter is selected from the group consisting of protonic acids, para toluene sulfonic acid, methane sulfonic acid, trifluoro methane sulfonic acid, acetic acid, formic acid, oxalic acid, and trifluoro acetic acid.

6. A catalyst system as claimed in claim 1 wherein the proton source is selected from the group consisting of water, formic acid, acetic acid and propionic acid for the preparation of α,β-unsaturated acids.

7. A catalyst system as claimed in claim 1 wherein the proton source is selected from the group of alcohols consisting of methanol, ethanol, butanol or phenol for the preparation of α,β-unsaturated esters.

8. A catalyst system as claimed in claim 1 wherein the concentration of palladium compound is 1 mole of palladium compound for every 100 to 5000 moles of alkyne.

9. A catalyst system as claimed in claim 1 wherein the concentration of the palladium compound used is one mole for every 200 to 1000 moles of alkyne.

10. A catalyst system as claimed in claim 1 wherein the number of moles of the anionic semilabile ligand per gram atom of palladium in the catalyst system is in the range of 1 to 100 moles.

11. A catalyst system as claimed in claim 1 wherein the number of moles of the anionic semilabile ligand per gram atom of palladium is in the range of 2 to 20 moles.

12. A catalyst system as claimed in claim 1 wherein the number of moles of acid promoter per gram atom of palladium in the catalyst system is in the range of 1 to 100 mole.

13. A catalyst system as claimed in claim 1 wherein the number of moles of acid promoter per gram atom of palladium is in the range of 10–40 in case of preparation of α,β-unsaturated esters.

14. A catalyst system as claimed in claim 1 wherein the number of moles of acid promoter per gram atom of palladium is in the range of 30–50 in case of preparation of α,β-unsaturated acids.

15. A catalyst system as claimed in claim 1 wherein the number of moles of the mono phosphorus ligand per gram atom of palladium in the catalyst system is in the range of 1 to 100 moles.

16. A catalyst system as claimed in claim 1 wherein the number of moles of the mono phosphorus ligand per gram atom of palladium in the catalyst system is in the range of 4 to 40 moles.

17. A catalyst system as claimed in claim 1 wherein the number of moles of proton source per mole of the alkyne is in the range of 1 to 50 moles.

18. A catalyst system as claimed in claim 1 wherein the number of moles of proton source per mole of the alkyne is in the range of 2 to 10 moles.

19. A process for the preparation of α,β-unsaturated carboxylic acids and their esters having the formula II (II)

wherein $R_1$ and $R_2$ represent hydrogen atom or an alkyl, aryl, arylalkyl, cycloaliphatic group with or without substituents, and $R_3$ represents a hydrogen atom in case of acids and represents aryl, alkyl, arylalkyl, cycloaliphatic group with or without substituents in case of esters, comprising the steps of:

I. reacting alkynes represented by the formula I (I)

wherein $R_1$ and $R_2$ have the meaning given above, with a compound containing palladium, in an aprotic organic solvent, in the presence of a catalyst system, comprising:
(a) a palladium metal source;
(b) a monodentate phosphorus ligand;
(c) anionic semilabile chelating ligand containing N-donor and an O group selected from the group consisting of 2-hydroxy pyrridine, (2-(2'-hydroxy ethyl pyrridine), pyridil-3, piperidil-2, quinolyl-2, isoquinolyl-3-carboxylic acids, pyridil-2, piperidil-2-carboxylic acids, 8-hydroxy quinoline, and pyridine carboxylic acid;
(d) acid promoter; and
(e) proton source;
wherein the rates of palladium:anionic semilabile ligand:phosphorus:acid promoter is in the range of 1:2:4:10 to 1:15:30:40 in a carbon monoxide atmosphere in a homogeneous medium, at a temperature ranging between 30 to 120° C., for a period ranging between 30 to 120 minutes at ambient pressure;

II. cooling the reaction mixture to ambient temperature;

III. flushing the reaction vessel with inert gas;

IV. removing the solvent by conventional methods;

V. separating the catalyst; and

VI. isolating the α,β-unsaturated carboxylic acids and their esters by conventional methods.

20. A process as claimed in claim 19 wherein an alcohol selected from the group consisting of methanol, ethanol, butanol, and phenol acts as the proton source.

21. A process as claimed in claim 20 wherein the aprotic organic solvent is selected from the group of hydrocarbons consisting of benzene, toluene, and xylene.

22. A process as claimed in claim 20 wherein the aprotic organic solvent is selected from the group of ketones consisting of methyl ethyl ketone, and acetone.

23. A process as claimed in claim 20 wherein the aprotic organic solvent is selected from the group of amides consisting of N-methyl pyrrolidone.

24. A process as claimed in claim 20 wherein the aprotic organic solvent used is selected from the group of nitriles consisting of acetonitrile.

25. A process as claimed in claim 20 wherein the aprotic organic solvent used is selected from the group of carboxylic acids consisting of formic acid, acetic acid and propionic acid.

26. A process as claimed in claim 20 wherein the reaction is carried out in a stirred reaction with a catalyst employed in a homogeneous phase in the aprotic organic solvent in the presence of carbon monoxide at ambient atmosphere pressure.

27. A process as claimed in claim 20 wherein the reaction is carried out at a pressure of 5–100 psig.

28. A process as claimed in claim 19 wherein the aprotic organic solvent used for the preparation of $\alpha,\beta$-unsaturated esters is selected from the group of organic compounds consisting of hydrocarbons, nitriles, carboxylic acids, aromatic hydrocarbons, ketones, amides and cyclic esters.

29. A process as claimed in claim 19 wherein the aprotic organic solvent is selected from the group of esters consisting of tetrahydrofuran and dioxane.

* * * * *